United States Patent [19]
East et al.

[11] Patent Number: 5,167,615
[45] Date of Patent: * Dec. 1, 1992

[54] FLOW CONTROL DEVICE HAVING SELECTABLE ALTERNATIVE FLUID PATHWAYS

[75] Inventors: Gary P. East, Santa Barbara; David A. Watson, Goleta, both of Calif.

[73] Assignee: Pudenz-Schulte Medical Research Corporation, Goleta, Calif.

[*] Notice: The portion of the term of this patent subsequent to Oct. 13, 2009 has been disclaimed.

[21] Appl. No.: 694,896

[22] Filed: May 2, 1991

Related U.S. Application Data

[63] Continuation-in-part of Ser. No. 524,136, May 15, 1990, Pat. No. 5,154,693.

[51] Int. Cl.⁵ ............................................. A61M 27/00
[52] U.S. Cl. ....................................... 604/9; 604/247; 137/854
[58] Field of Search ............................. 604/8-10, 604/247, 186; 137/854

[56] References Cited

U.S. PATENT DOCUMENTS

| | | | |
|---|---|---|---|
| 4,552,553 | 11/1985 | Schulte et al. | |
| 4,560,375 | 12/1985 | Schulte et al. | 604/9 |
| 4,636,194 | 1/1987 | Schulte et al. | |
| 4,741,230 | 5/1988 | Dormandy, Jr. et al. | 604/8 |
| 4,761,158 | 8/1988 | Schulte et al. | 604/9 |
| 4,781,673 | 11/1988 | Watanabe | 604/9 |
| 4,781,674 | 11/1988 | Ridmond et al. | 604/9 |
| 4,795,437 | 1/1989 | Schulte et al. | 604/10 |
| 4,850,955 | 7/1989 | Newkirk | 604/9 |
| 4,861,331 | 8/1989 | East et al. | 604/9 |
| 4,867,740 | 9/1989 | East | 604/9 |
| 4,867,741 | 9/1989 | Potnay | 604/10 |
| 4,995,864 | 2/1991 | Bartholemew et al. | 604/9 |

Primary Examiner—Robert A. Hafer
Assistant Examiner—Kerry Owens
Attorney, Agent, or Firm—Kelly, Bauersfeld & Lowry

[57] ABSTRACT

A flow control device for use in a subcutaneously implanted physiological shunt system includes a relatively rigid base and a resiliently flexible encasement which defines a fluid flow path therethrough from an inlet to an outlet. Two valves for controlling the flow of fluid through the device are situated within the fluid flow path between the inlet and the outlet. The fluid flow path includes a first fluid conduit which directs fluid through both valves, and a second fluid conduit which bypasses the first valve and directs fluid only through the second valve. The first valve is constructed to provide a greater resistance to flow through the device than the second valve, and when the second fluid conduit is unobstructed, fluid will tend to flow through the second fluid conduit and bypass the first valve. A pivotable plug is provided within the encasement for selectively occluding a portion of the second fluid conduit. The position of the plug is determined by a magnetically polarized, percutaneously manipulable cam also provided within the encasement. The plug and the cam are attached such that rotation of the cam in one direction causes the plug to occlude the second fluid conduit, and rotation of the cam in another direction opens the second fluid conduit to fluid flow. A siphon control device is provided adjacent to the outlet to prevent fluid flow in response to negative downstream hydrostatic pressure on the outlet of the device.

24 Claims, 3 Drawing Sheets

5,167,615

FLOW CONTROL DEVICE HAVING SELECTABLE ALTERNATIVE FLUID PATHWAYS

RELATED APPLICATION

This is a continuation-in-part application of U.S. patent application Ser. No. 07/524,136, filed May 15, 1990, now U.S. Pat. No. 5,154,693, and entitled FLOW CONTROL DEVICE HAVING SELECTABLE ALTERNATIVE FLUID PATHWAYS.

BACKGROUND OF THE INVENTION

This invention relates generally to surgically implanted physiological shunt systems and related flow control devices. More particularly, the present invention relates to shunt systems including one-way flow control valves for controlling the flow of cerebrospinal fluid out of a brain ventricle and preventing backflow of fluid into the brain ventricle.

In the medical arts, to relieve undesirable accumulation of fluids it is frequently necessary to provide a means for draining a fluid from one part of the human body to another in a controlled manner. This is required, for example, in the treatment of hydrocephalus, a ailment usually afflicting infants or children in which fluids accumulate within the skull and exert extreme pressure and skull deforming forces.

In treating hydrocephalus, cerebrospinal fluid accumulated in the brain ventricles is typically drained away utilizing a drainage or shunt system including a catheter inserted into the ventricle through the skull, which is connected to a tube that conducts the fluid away from the brain to be reintroduced into the peritoneal cavity or into the vascular system, as by extending a distal catheter through the patient's jugular vein to the atrium portion of the heart. To control the flow of cerebrospinal fluid and maintain the proper pressure in the brain ventricle, a pump or valve is placed in the conduit between the brain and the peritoneal cavity or the heart. An exemplary flow control device is found in U.S. Pat. No. 4,560,375.

Although such drainage systems have provided successful results, a problem of over drainage of the cerebrospinal fluid from the brain ventricles sometimes exists. Over drainage of cerebrospinal fluid may result in excessive reduction of the cerebrospinal fluid pressure within the brain ventricles and predispose the development of a subdural hematoma or hydroma, and excessive reduction of ventricular size leading to shunt obstruction because of impingement of the ventricular walls on the inlet holes of the ventricular catheter. This over drainage can be caused by the siphoning effect of hydrostatic pressure in the distal shunt catheter. The siphoning effect of hydrostatic pressure may be created by the elevation of the ventricular catheter inlet with respect to the distal catheter outlet (i.e., when the patient sits, stands or is held erect). In order to prevent such over drainage caused by the siphoning effect of hydrostatic pressure in the distal shunt catheter, siphon control devices have been placed in the conduit, typically between the flow control device and the peritoneal cavity or the heart. An exemplary siphon control device is found in U.S. Pat. No. 4,795,437.

It is desirable in some instances to permit the physician to be able to alter the flow characteristics through the drainage system after it has been subcutaneously implanted. To this end, on-off devices have been provided for implantation as a portion of the fluid conduit, as an additional element of the shunt. An exemplary on-off device is shown in U.S. Pat. No. 3,827,439.

Prior physiological shunt systems have failed to provide, however, a flow control device which permits only unidirectional flow through the shunt system, prevents over drainage caused by the siphoning effect of hydrostatic pressure in the distal shunt catheter, and permits the flow characteristics through the shunt to be altered percutaneously after the shunt system has been surgically implanted. Further, existing flow control devices extensively used in connection with the treatment of hydrocephalus typically provide only a single pre-set resistance to the flow of excess cerebrospinal fluid through the shunt system, which cannot be varied except to prevent fluid flow through the shunt by means of an on-off valve.

Accordingly, there has been a continuing need in the medical arts for convenient and effective physiological drainage devices for controlling the flow of fluid from one part of the body to another, which are relatively inexpensive to manufacture and can be constructed substantially of non-metallic parts which are not subject to adhering to one another and causing a malfunction of the device. A flow control device is needed which permits fluid flow therethrough only when upstream fluid pressure exceeds downstream fluid pressure by a selected pressure differential, and which also provides means for altering the selected pressure differential by percutaneous manipulation of the device when it is subcutaneously implanted.

Additionally, a novel flow control device for use in a physiological shunt system is needed which utilizes a plurality of flow control valves having different flow control characteristics. Such a device should provide alternative fluid pathways therethrough such that selection of the desired fluid pathway can be made by the selective percutaneous manipulation of the device when it is subcutaneously implanted. Moreover, such a flow control device is needed which incorporates an integral siphon control device that opens only in response to positive upstream fluid pressure, and recloses or remains closed in the absence of such positive upstream fluid pressure or in response to negative downstream hydrostatic pressure on the device. As will become apparent from the following description, the present invention satisfies these needs and provides other related advantages.

SUMMARY OF THE INVENTION

The present invention resides in a physiological shunt system for controlling the flow of fluid from one part of the body to another, which is constructed substantially of non-metallic materials and provides trouble-free and reliable operation in use. The shunt system of the present invention is relatively inexpensive to manufacture, and can be easily modified to provide a variety of pressure/flow characteristics. In accordance with the present invention, a flow control device for use in a subcutaneously implanted physiological shunt system includes a housing having an inlet and an outlet, a fluid flow path through the housing from the inlet to the outlet, and means for controlling fluid flow through the fluid flow path. The controlling means includes means for permitting fluid flow through the fluid flow path when upstream fluid pressure exceeds downstream fluid pressure by a selected pressure differential, and means for altering the selected pressure differential by percutaneous manipulation of the flow control device when it is subcutaneously implanted.

In a preferred form of the invention, the controlling means includes a first normally closed valve which opens to permit fluid flow through the fluid flow path when upstream fluid pressure exceeds downstream fluid pressure by a first pressure differential, and a second normally closed valve which opens to permit fluid flow through the fluid flow path when upstream fluid pressure exceeds downstream fluid pressure by a second pressure differential. Preferably, the first pressure differential is greater than the second pressure differential.

The fluid flow path includes a first fluid conduit for directing fluid through the first and second normally closed valves, and a second fluid conduit which bypasses the first normally closed valve and directs fluid through the second normally closed valve only. The means for altering the selected pressure differential comprises means for selectively directing fluid either through the first or second fluid conduits.

The first and second normally closed valves each include a base having a valve passageway therethrough, and a valve seat surrounding a portion of the valve passageway. A flow control member contacts the valve seat in a manner normally occluding the valve passageway, but selectively opens to permit controlled unidirectional flow therethrough. Each flow control member includes a central support and a resilient membrane. The central support is attached to the base and extends therefrom to support the resilient membrane. The resilient membrane is generally arch-shaped and has a portion thereof capable of engaging the valve seat to occlude the valve passageway.

A variety of pressure/flow characteristics can be provided by the flow control device of the present invention by manufacturing the normally closed valves with different resilient membranes of varying thicknesses. The resistance to flow past a normally closed valve increases with an increase in membrane thickness.

The means for selectively directing fluid either through the first or second fluid conduits includes means for occluding the second fluid conduit means. This occluding means includes a selectably positionable plug movable between a first position wherein the second fluid conduit is open to fluid flow therethrough, and a second position wherein the second fluid conduit is closed to fluid flow therethrough. The occluding means further includes a magnetically polarized, percutaneously manipulable cam which is rotatable between a first position and a second position. The plug has an occluder at one end and a cam rider at another end. The cam rider interacts with the cam such that rotation of the cam between its first and second positions simultaneously moves the plug between its first and second positions to, selectively, open and close a portion of the second fluid conduit to fluid flow therethrough.

In order to provide the desired resistance to adhesion between various components of the flow control device, particularly during storage, rigid components of the valve are generally formed of a rigid polypropylene material, while elastic components, such as the valve resilient membranes, are preferably molded of a silicone elastomer material.

An intermediate fluid passageway between the first and second normally closed valves is configured to provide a flushing reservoir, and integral flow occluders are provided generally adjacent to the inlet and the outlet, all of which are operated by percutaneous finger pressure applied to the device. Through selective application of percutaneous pressure to the flow occluders and the flushing reservoir, fluid within the reservoir can be selectively flushed both proximally and distally through the device.

A siphon control device is situated between the second normally closed valve and the outlet, to prevent fluid flow through the flow control device in the absence of positive upstream fluid pressure or in response to negative downstream hydrostatic pressure. The siphon control device comprises an integral housing including a pair of spaced, substantially parallel, flexible diaphragms, and a base invested within the housing.

Other features and advantages of the present invention will become apparent from the following more detailed description, taken in conjunction with the accompanying drawings which illustrate, by way of example, the principles of the invention.

BRIEF DESCRIPTION OF THE DRAWINGS

The accompanying drawings illustrate the invention. In such drawings.

DETAILED DESCRIPTION OF THE PREFERRED EMBODIMENT

As shown in the drawings for purposes of illustration, the present invention is concerned with an improved flow control device, generally designated in the accompanying drawings by reference number 10. The improved flow control device 10 is intended for use in a surgically implanted physiological shunt system for draining fluid from one portion of the body to another. In order to connect, for example, the device 10 in such a system, the device includes an inlet connector 12 and an outlet connector 14 which each receive one end of a piece of surgical tubing (not shown). The ends of the surgical tubing are placed over the connectors 12 and 14 and secured thereon by a single ligature just inside of an annular ridge 16 formed near the end of each connector.

When the flow control device 10 is used in a drainage system intended for the treatment of hydrocephalus, the inlet connector 12 is fluidly connected with a proximal catheter which is inserted through the skull into a brain ventricle containing cerebrospinal fluid under pressure. The outlet connector 14 is fluidly connected to a distal catheter which serves to discharge cerebrospinal fluid into, for example, the atrium portion of a patient's heart. Ordinarily the flow control device 10 will be surgically implanted on the patient's skull with a flap of skin overlying the device. To facilitate holding the device in its desired position after implantation, a generally flexible mounting plate 18 can be provided with one or more suture holes.

As will become apparent from the following description, the present invention provides a highly reliable flow control device having selectable alternative fluid pathways which permit the flow control characteristics of the device 10 to be altered when subcutaneously implanted by percutaneous manipulation of the device. The present invention provides a highly reliable flow control device designed to prevent valve seat deformation and membrane to valve seat sticking, and to facilitate implantation by eliminating components to be connected or adjusted other than the surgical tubing to the device itself.

In accordance with the present invention, the flow control device 10 includes a pair of relatively rigid, molded, plastic bases 20 and 22 invested within a resiliently flexible housing 24 which, together, define a fluid flow path through the housing from the inlet connector 12 to the outlet connector 14. Two normally closed valves 26 and 28 are provided within the fluid flow path to restrict the flow of fluid through the device 10. The housing 24 and the second base 22 cooperate to provide a siphon control device 30, situated between the second valve 28 and the outlet connector 14, which prevents fluid flow through the device 10 in the absence of positive upstream fluid pressure or in response to negative downstream hydrostatic pressure on the device. Further, the housing 24 and the first base 20 cooperate to define a pump or flushing reservoir 32 between the inlet connector 12 and the second valve 28.

Two alternative fluid conduits, defining portions of the fluid flow path through the device 10, are provided in order to permit the flow control characteristics of the device 10 to be altered by percutaneous manipulation of the device when it is subcutaneously implanted. A first fluid conduit 34 directs fluid through both the first and second normally closed valves 26 and 28. A second fluid conduit 36 bypasses the first normally closed valve 26 and directs fluid through the second normally closed valve 28 only.

More specifically, and as shown best in FIGS. 2-5, the bases 20 and 22 interfit with one another and are integrally formed with, respectively, the inlet and outlet connectors 12 and 14. The first or proximal base 20 defines an inlet flow channel 38 extending through the inlet connector 12 to a first valve housing 40 in which the first normally closed valve 26 is positioned. The first base 20 also forms a bottom plate 42 for the flushing reservoir 32, a second valve housing 44 for supporting the second normally closed valve 28, and a snap-fit interlocking barbed connector 46.

Each of the valve housings 40 and 44 include a valve support plate 48 having a centrally positioned valve-supporting aperture 50, and three surrounding apertures 52 which permit fluid flow through the supports 48. Adjacent to each of the supports 48, the valve housings 40 and 44 define generally cylindrical valve chambers 54 into which the valves 26 and 28 extend. After the first valve 26 is secured within the first valve housing 40, a first valve housing cap 56, having two apertures 58 therethrough, is securely fixed to the base 20 opposite the support 48 to enclose the first valve 26 within its valve chamber 54. After the second valve 28 is secured within the second valve housing 44, a second valve housing cap 60 is securely fixed to the base 20 opposite to the support 48 to enclose the second valve within its valve chamber 54. An intermediate flow channel 62 extends from the second valve chamber 54 through the connector 46 to direct fluids from the first base 20 to the second base 22.

Figure 5:
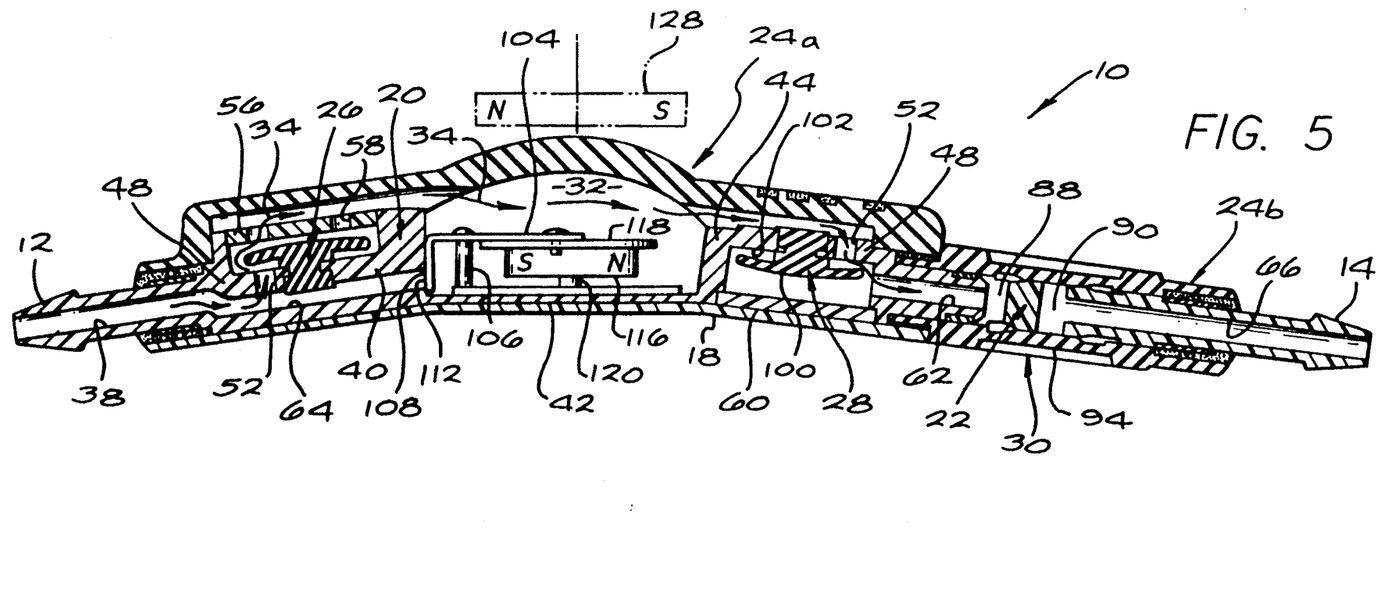
FIG. 5 is a vertical sectional view similar to that illustrated in FIGS. 2 and 4, illustrating the manner in which fluid flows through the flow control device past both the first and second valves when the second fluid conduit is occluded.

As shown best in FIG. 5, the fluid flow path extending from the inlet flow channel 38 upwardly through the apertures 52, past the first valve 26, and then through the apertures 58 of the housing cap 56 comprises a portion of the first fluid conduit 34. A bypass conduit 64 extends beneath the support 48 of the first valve housing 40 between the inlet flow channel 38 and the flushing reservoir 32.

The barbed connector 46 extends from the first base 20 generally opposite to the inlet connector 12. A pair of splines (not shown) extend from the first base 20 adjacent to the connector 46 and, together with the connector 46, interact with corresponding portions of the second base 22 to prevent tensile and torsional movement of the proximal and distal bases 20 and 22 with respect to one another.

The second or distal base 22 is integrally formed with the outlet connector 14 which defines an outlet flow channel 66 therethrough. The second base 22 defines a portion of the siphon control device 30. A connector receptacle 68 is provided in the proximal end of the second base 22 for receiving the barbed connector 46 therein. Spline receiving slots (not shown) are also provided in the proximal end of the second base, to slidably receive and substantially envelope the splines as the connector 46 is inserted into the receptacle 68.

The flexible housing 24 is provided in two parts: a first or inlet housing body 24a into which the first base 20 is invested, and an outlet or second housing body 24b which is sealed by a suitable adhesive 70 to the inlet housing body 24a in order to provide a continuous elastomeric exterior to the device 10, with the exception of the inlet and outlet connectors 12 and 14 which extend therefrom. The inlet housing body 24a is integrally formed with the mounting pad 18 and includes an inlet aperture through which the inlet connector 12 extends, an inlet occluder wing 72 which generally overlies the first valve housing cap 56, a resiliently flexible dome 74 for the flushing reservoir 32, and a distal occluder wing 76 generally overlying the support 48 of the second valve housing 44.

In order to provide a fluid-tight seal between the inlet connector 12 and the housing 24a, a tube 78 is placed over a portion of the inlet connector and secured in place by means of an over-suture 80. A silicone adhesive 82 is then injected into the remaining gap between the housing 24a and the inlet connector 12. This same sealing arrangement is utilized between the housing 24b and the outlet connector 14.

The inlet occluder wing 72 is positioned over the apertures 58 of the first valve housing cap 56 to facilitate occluding a portion of the first fluid conduit 34 by pressing the wing 72 downwardly. Depressing the wing 72 and occluding the apertures 58, when the bypass conduit 64 is also occluded, prevents proximal fluid flow from the flushing reservoir 32, defined by the dome 74 and the bottom plate 42, when the dome is pressed downwardly by manual percutaneous pressure. The dome 74 is preferably molded of a silicone elastomer material and is designed to permit injection into the flow control device 10 by a hypodermic needle through the dome. The bases 20 and 22 are preferably molded of a polypropylene material which provides sufficient rigidity to prevent a needle from inadvertently passing through the device 10 if an injection is made into the flushing reservoir 32. The construction of the bases 20 and 22 and the housing 24 helps to guide a physician in manually percutaneously manipulating the device 10 when subcutaneously implanted, for purposes of flushing the shunt system.

The distal occluder wing 76 is positioned over the support 48 of the second valve housing 44 to facilitate occluding the apertures 52 therethrough. This is accomplished by pressing the wing 76 downwardly, which effectively prevents distal fluid flow from the flushing reservoir 32 when the dome is pressed downwardly by manual percutaneous pressure.

The outlet housing body 24b surrounds a portion of the second base 22 to define the siphon control device 30 which is similar to that shown and described in U.S. Pat. No. 4,795,437, the contents of which are incorporated herein by reference. The siphon control device 30 includes an outer wall 84 and an inner wall 86 which is situated within and encircled about by the outer wall. The intermediate flow channel 62 directs fluid from the valve chamber 54 of the second valve housing 44 to a central SCD reservoir 88 defined as the area between the inner wall 86 and the outer wall 84. The outlet flow channel 66 extends through the inner wall 86 to the distal end of the outlet connector 14.

Figure 3:
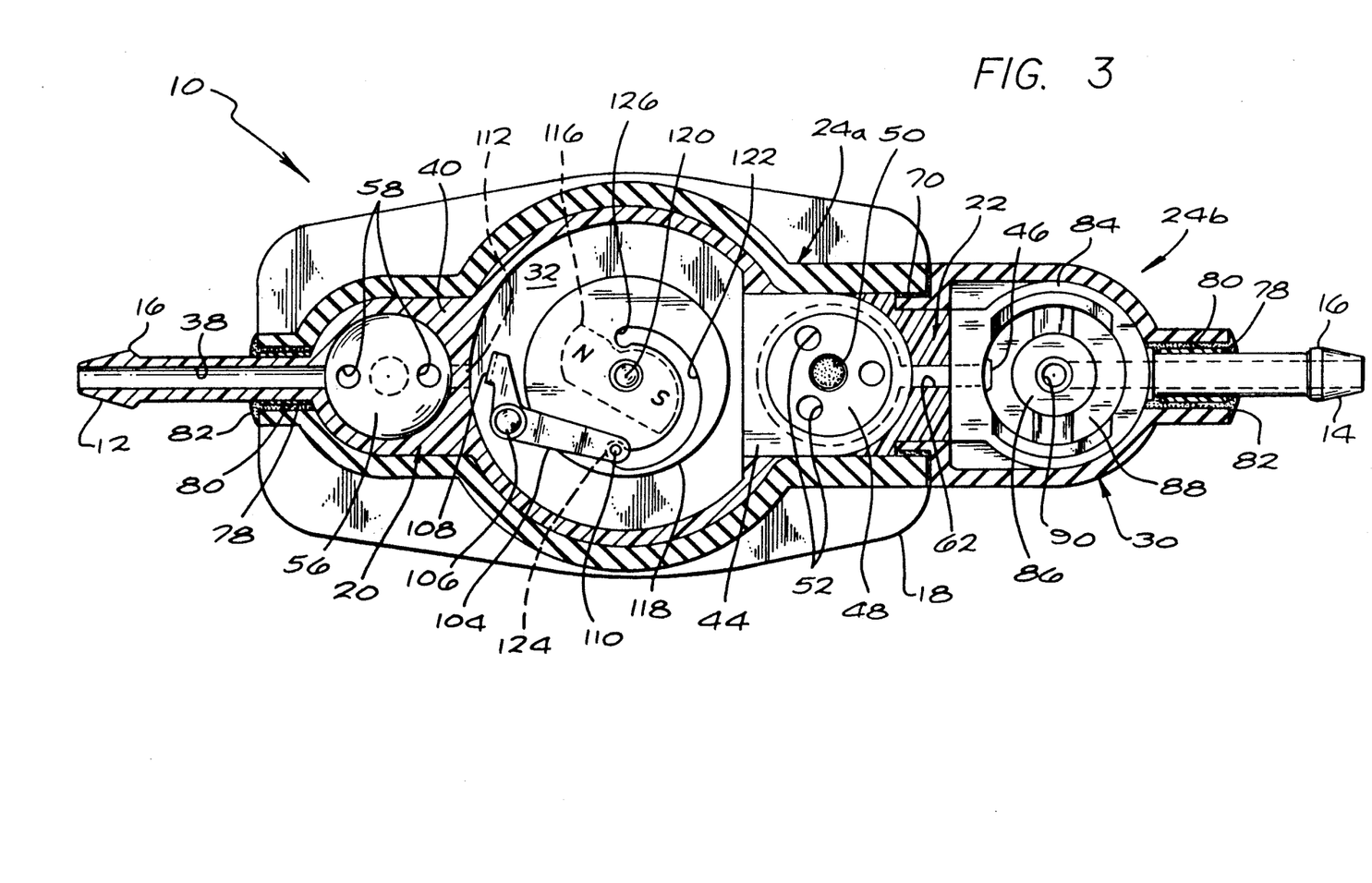
FIG. 3 is a horizontal section taken generally along the line 3—3 of FIG. 2, illustrating the configuration of the flow control device when the second fluid conduit is open to fluid flow.

As can be best seen in FIG. 3, the outer wall 84 is generally circular in shape, and is spaced from and encircles the inner wall 86. The inner wall is also generally circular in shape, and defines an SCD outlet chamber 90 which is adjacent to and in fluid communication with the outlet flow channel 66. The inner wall 86 is constructed to have substantially parallel upper and lower seating surfaces 92, and it effectively forms a barrier separating the SCD reservoir 88 from the SCD outlet chamber 90.

The outlet housing body 24b is provided with a pair of spaced, substantially parallel, flexible elastic diaphragms 94 which are fixed about their peripheries adjacent to the outer wall 84. Each diaphragm has an inner surface which defines the upper and lower limits of the SCD reservoir 88 and the SCD outlet chamber 90, and an outer surface which forms an exterior surface of the siphon control device 30. The diaphragms 94 are situated on opposite sides of the inner wall 86 to position a portion of each inner surface thereof in contact with an adjacent one of the seating surfaces 92 and form a seal therebetween which prevents fluid flow between the intermediate flow channel 62 and the outlet flow channel 66.

The second housing body 24b further includes integral offset rings 96 which surround each diaphragm 94 to inhibit overlying tissue from occluding the siphon control device 30 when implanted into a patient. An aperture is provided through the housing 24b through which the outlet connector 14 extends. A fluid tight seal is effected between the housing outlet aperture and the outlet connector 14 utilizing a tube 78, an over-suture 80 and an adhesive 82, as described above in connection with the inlet housing body 24a and the inlet connector 12.

In use, the diaphragms 94 normally lie against and interact with the seating surfaces 92 of the inner wall 86 to close the device 10 to fluid flow. The diaphragms 94 move away from the seating surfaces 92, however, in response to a minimal level of positive fluid pressure within the SCD reservoir 88 to permit passage of fluid from the intermediate flow channel 62 to the outlet flow channel 66. The diaphragms 94 close and seal upon the seating surfaces 92 once again in the absence of such positive upstream fluid pressure, or in response to negative downstream hydrostatic pressure in the SCD outlet chamber 90. The siphon control device 30 thus minimizes the undesirable consequences attendant to excessive overdrainage of fluid due to the siphoning effect of hydrostatic pressure.

Each of the normally closed valves 26 and 28 extend from their respective supports 48 into the valve chambers 54 of the first and second valve housings 40 and 44, respectively, for controlling the flow of cerebrospinal fluid out of a brain ventricle. Each normally closed valve 26 and 28 comprises a flow control member, including a central support 98 and a resilient membrane 100 molded of a synthetic polymer material different from the material of the first base 20. The resilient membrane 100 is normally biased to close communication between the inlet flow channel 38 and the intermediate flow channel 62, but will open to permit flow through the adjacent apertures 52 when the pressure on the inlet or proximal side of the resilient membrane exceeds the pressure on the outlet or distal side by a predetermined amount. Moreover, should the pressure on the distal side of the resilient membrane 100 ever exceed the pressure on the proximal side, tending to cause flow in a reverse direction through the normally closed valves 26 and 28, the membrane 100 will seal tightly against a valve seat 102 provided on the adjacent support 48, to prevent any such reverse fluid flow.

The first or proximal base 20 is preferably formed of a polypropylene material, and the membrane 100 is preferably formed of a silicone elastomer material. Both polypropylene and elastomer materials have been shown to produce an acceptable level of tissue reaction, and the use of this particular duality of materials, in contrast to the use of only a single material, markedly decreases the chances of the membrane 100 adhering to any portion of the valve seat 102 which would clog the fluid pathway through the device 10 and defeat the purpose of the device.

The membrane 100 has an arch-shape, as for example a second of a sphere, and is designed to contact the valve seat 102 generally along the outer edges of the membrane in a manner surrounding the apertures 52. The membrane 100 is secured in place adjacent to the valve seat 102 by the central support 98 which is fixed within the valve-supporting aperture 50 through each support 48.

Since the valves 26 and 28 are primarily designed to provide controlled resistance to cerebrospinal fluid flow from a brain ventricle to another location in the body, it will be appreciated that a doctor must be able to select valves having the particular pressure/flow characteristics desired for each individual application. That is, a valve which permits flow at a relatively low pressure differential may not be suitable where the maintenance of a higher pressure differential is indicated. Toward this end, in order to provide a flow control device with a variety of different pressure/flow characteristics, the first normally closed valve 26 has a different pressure/flow characteristic than the second normally closed valve 28. More particularly, the first normally closed valve 26 is provided with a relatively thick membrane 100, whereas the second normally closed valve 28 is provided a relatively thin membrane 100.

Resistance to flow increases with an increase in membrane thickness. Thus, the first normally closed valve 26 provides a higher degree of resistance to flow through the device 10 than the second normally closed valve 28.

Recognizing that fluid will tend to take the path of least resistance, it can be seen that fluid permitted to flow through the second fluid conduit 36, thereby bypassing the first normally closed valve 26, will experience a lesser degree of resistance to flow than if caused to flow through the first fluid conduit 34. FIGS. 1 through 4 illustrate the configuration of the flow control device 10 wherein the second fluid conduit 36 is open to fluid flow therethrough. If the bypass conduit 64 within the first base 20 below the first valve housing 40 is unoccluded, fluid is permitted to flow from the inlet flow channel 38 directly into the flushing reservoir 32 for introduction on the inlet or proximal side of the second normally closed valve 28. Since both of the normally closed valves 26 and 28 prevent retrograde fluid flow, the fluid passes only through the second normally closed valve 28 into the intermediate flow channel 62. Accordingly, resistance to flow through the flow control device 10 when the second fluid conduit 36 is open, is determined primarily by the second normally closed valve 28. From the intermediate flow channel 62, the fluid then passes through the siphon control device 30 to the outlet flow channel 66, for delivery to a distal catheter.

Figure 1:
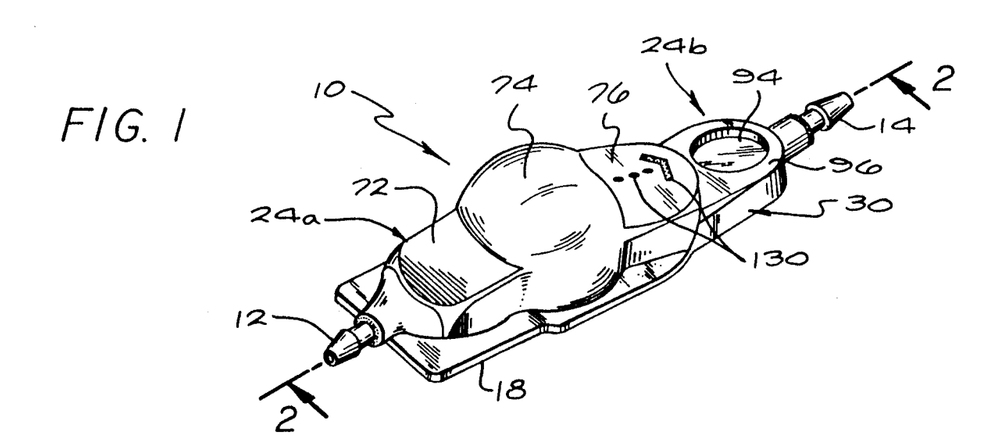
FIG. 1 is a perspective view of a flow control device having selectable alternative fluid pathways, embodying the invention.
Figure 2:
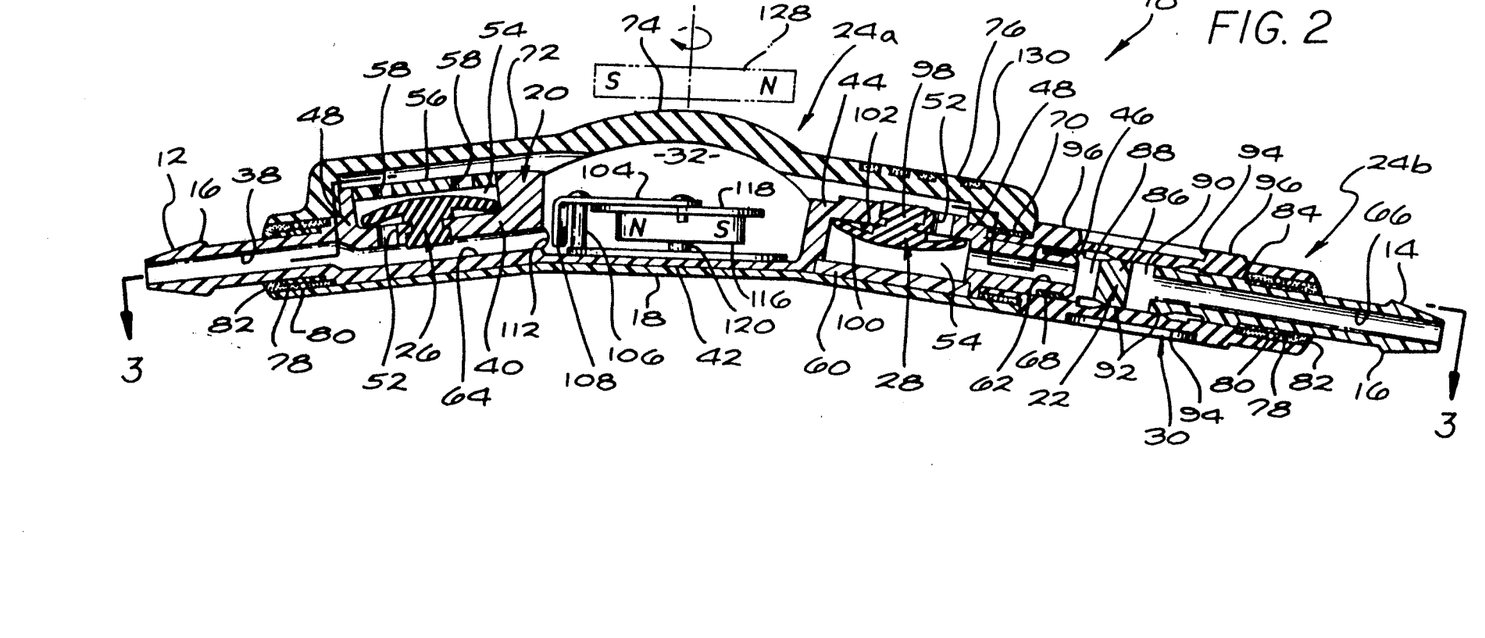
FIG. 2 is an enlarged vertical section taken generally along the line 2—2 of FIG. 1.
Figure 4:
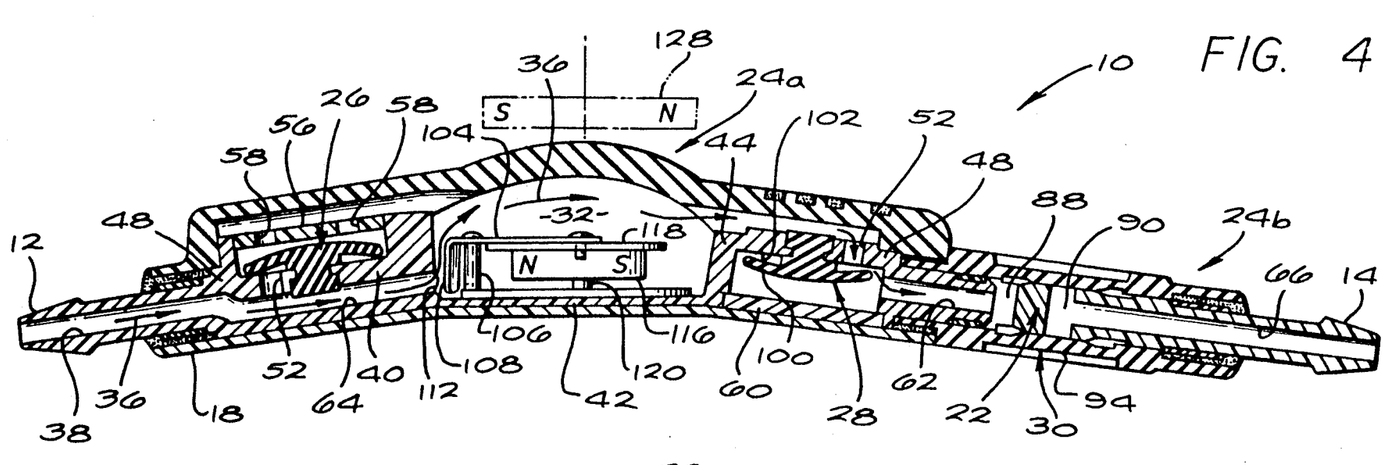
FIG. 4 is a vertical sectional view similar to that illustrated in FIG. 2, illustrating the manner in which fluid flows through the flow control device, bypassing a first valve and then past a second valve when the second fluid conduit is open to fluid flow therethrough.

In order to close the second fluid conduit 36 and thereby cause fluid passing through the device 10 to pass through both the first and second valves 26 and 28, means are provided for occluding the bypass conduit 64. More specifically, a selectively positionable plug 104 is pivotally mounted to a plug support 106 which extends upwardly from the bottom plate 42. The plug 104 includes an occluder 108 at one end and a cam rider 110 at another end. The occluder 108 is configured to permit fluid flow through the bypass conduit 64, and particularly an outlet aperture 112, when the plug 104 is pivoted into a first position (FIGS. 2-4). Alternatively, the plug 104 may be pivoted into a second position (FIG. 5), wherein the occluder 108 overlies and occludes the outlet aperture 112, thereby closing the bypass conduit 64 to fluid flow therethrough.

In order to selectively position the plug 104 within the flushing reservoir 32, a magnetically polarized, percutaneously manipulable cam 114 is also situated within the flushing reservoir 32. The cam 114 includes a permanent magnet 116 having well defined north and south poles. The permanent magnet 116 is mounted to the underside of a disc 118 which, in turn, is rotatably mounted upon a cam support shaft 120 that extends upwardly from the bottom plate 42. The disc 118 is provided with an arcuate slot 122 extending through approximately a 180° angle. A first end 124 of the slot 122 is situated adjacent to the outer periphery of the disc 118, while a second end 126 of the slot is situated much closer to the center of the disc.

The cam rider 110 of the plug 104 is situated within the slot 122. As illustrated in FIG. 2-4, when the cam rider 110 is positioned within the first end 124 of the slot 122, the plug 104 is pivoted about the plug support 106 to space the occluder 108 from the outlet aperture 112 of the bypass conduit 64. As the cam 114 is rotated clockwise when viewed from the perspective of FIG. 3, the cam rider 110 is drawn toward the center of the disc 118 which causes the plug 104 to pivot in a manner causing the occluder 108 to move toward the aperture 112. When, finally, the cam rider 110 is positioned within the second end 126 of the slot 122, the occluder 108 of the plug 104 is positioned directly against the portion of the base 20 surrounding the outlet aperture 112 in a manner preventing fluid flow through the bypass conduit 64 and thereby occluding the second fluid conduit 36.

With the second fluid conduit 36 so occluded by the plug 104, fluid entering the inlet flow channel 38 must pass through both the first and second normally closed valves 26 and 28 before exiting the device 10 through the outlet flow channel 66. Further, since the first normally closed valve 26 provides a greater degree of resistance to flow than the second normally closed valve 28, the first valve 26 primarily determines the resistance to flow of the device 10 in this configuration.

Subsequently, when it is desired to permit fluid flow through the outlet aperture 112 of the bypass conduit 64, the disc 118 is simply rotated in a counterclockwise direction to pivot the plug 104 away from the outlet aperture. Counterclockwise rotation of the disc 118 moves the cam rider 112 toward the periphery of the disc 118 as it follows the slot 122, until the cam rider is once again positioned in the first end 124 of the slot.

The permanent magnet 116 secured to the underside of the disc 118 permits the cam 114 to be rotated, as described above, by percutaneous manipulation thereof when the device 10 is subcutaneously implanted. In particular, a medical professional may turn the cam 114 by placing a magnetically polarized ring 128 (schematically illustrated in FIG. 2) directly over the flushing reservoir 32 of the device 10. With the knowledge that clockwise rotation of the cam 114 will cause occlusion of the second fluid conduit 36, and counterclockwise rotation of the cam will cause the second fluid conduit to be open to fluid flow, the polarized ring 128 is simply placed next to the skin and rotated in the direction intended to cause the desired flow path configuration. It does not matter how the polarized ring 128 is initially oriented over the flushing reservoir 32 of the device 10, because as the ring 128 is rotated in the desired direction, the magnetic poles of the ring will seek the opposite poles of the permanent magnet 116. When the polarized ring 128 is aligned with the permanent magnet 116 as shown in FIG. 2, further rotation of the ring will tend to cause like rotation of the cam 114 until the cam rider 110 is positioned in either the first or second ends 124 and 126 of the slot 122.

The design of the flow control device 10, permits percutaneous distal and proximal flushing of fluid within the fluid reservoir 32 by percutaneous manipulation when the device is subcutaneously implanted. In order to flush the device 10 distally, the cam 114 is first rotated clockwise in order to occlude the second fluid conduit 36. The inlet occluder wing 72 is pressed downwardly to occlude the apertures 58 through the first valve housing cap 56. The dome 74 is then simply pressed downwardly to flush the contents of the flushing reservoir 32 through the second valve housing 44, past the siphon control device 30 and through the outlet flow channel 66. Similarly, proximal flushing can be accomplished by first turning the cam 114 counterclockwise to open the bypass conduit 64 to fluid flow therethrough, and by pressing downwardly on the distal occluder wing 76, to occlude the apertures 52 of the second valve housing 44. The dome 74 is then pressed downwardly to flush fluid proximally from the flushing reservoir 32 out of the device 10 through the bypass conduit 64 and the inlet flow channel 38.

From the foregoing it is to be appreciated that the present invention provides a flow control device 10 for use in a subcutaneously implanted physiological shunt system having selectable alternative means for controlling fluid flow through the fluid flow path. Through the provision of a first fluid conduit 34 which directs fluid through both the first and second normally closed valves 26 and 28, and an alternative second fluid conduit 36 which bypasses the first normally closed valve 26, means are provided for permitting fluid flow when upstream fluid pressure exceeds downstream fluid pressure by two different selected pressure differentials. The construction of the flow control device 10 of the present invention permits selective distal and proximal flushing of the device through the application of manual percutaneous pressure, and further permits the selected pressure differential to be altered, also through percutaneous manipulation of the device when subcutaneously implanted. The present invention provides a device by which the flow of cerebrospinal fluid out of a brain ventricle can be controlled while preventing the backflow of fluid into the brain ventricle, and inhibits excessive drainage through the physiological shunt in the presence of excessive downstream suction. Radiopaque indicators 130 may also be provided to provide X-ray detectable indicators of valve type and flow direction.

Although a particular embodiment of the invention has been described in detail for purposes of illustration, various modifications may be made without departing from the spirit and scope of the invention. Accordingly, the invention is not to be limited, except as by the appended claims.

We claim:

1. A fluid flow control device, comprising:
   a housing having an inlet and an outlet;
   a first fluid flow pathway through the housing from the inlet to the outlet, the first fluid flow pathway having first means including a first valve for resisting fluid flow therethrough;
   a second fluid flow pathway through the housing from the inlet to the outlet, the second fluid flow pathway having second means including a second valve for resisting fluid flow therethrough, wherein the first fluid flow pathway directs fluid through the first and second valves, and the second fluid flow pathway bypasses the first valve and directs fluid through the second valve; and
   means for selectively directing fluids through one of the first or the second fluid flow pathways, the fluid directing means being actuable by percutaneous manipulation of the device when subcutaneously implanted.

2. A fluid flow control device as set forth in claim 1, wherein the first and second valves each comprise a base including a valve passageway therethrough and a valve seat surrounding a portion of the valve passageway, and a flow control member contacting the valve seat in a manner normally occluding the valve passageway but selectively opening to permit controlled unidirectional flow therethrough.

3. A fluid flow control device as set forth in claim 2, wherein each flow control member includes a central support and a resilient membrane, the central support being attached to the respective base and extending therefrom to support the resilient membrane, the resilient membrane being generally arch-shaped and having a portion thereof capable of engaging the respective valve seat to occlude the respective valve passageway.

4. A fluid flow control device as set forth in claim 1, wherein the first valve provides a greater resistance to flow than the second valve.

5. A fluid flow control device as set forth in claim 1, wherein the means for selectively directing fluids through either the first or the second fluid flow pathways includes means for occluding the second fluid flow pathway.

6. A fluid flow control device as set forth in claim 5, wherein the means for occluding the second fluid flow pathway includes a selectively positionable plug movable between a first position wherein the second fluid flow pathway is open to fluid flow therethrough, and a second position wherein the second fluid flow pathway is closed to fluid flow therethrough.

7. A fluid flow control device as set forth in claim 6, wherein the means for occluding the second fluid flow pathway includes a magnetically polarized, percutaneously manipulable cam rotatable between a first position and a second position, the plug having an occluder at one end and a cam rider at another end, wherein the cam rider interacts with the cam such that rotation of the cam between its first and second positions simultaneously moves the plug between its first and second positions.

8. A fluid flow control device as set forth in claim 1, including a pump between the inlet and the outlet, wherein the pump provides means for flushing fluid from the fluid flow control device by application of percutaneous manual pressure to the device.

9. A fluid flow control device as set forth in claim 8, including means for temporarily occluding a portion of the fluid flow pathways adjacent to the inlet by application of percutaneous manual pressure to the housing such that actuation of the pump flushes fluid distally through the device.

10. A fluid flow control device as set forth in claim 8, including means for temporarily occluding a portion of the fluid flow pathways adjacent to the outlet by application of percutaneous manual pressure to the housing such that actuation of the pump flushes fluid proximally through the device.

11. A fluid flow control device as set forth in claim 1, including siphon control device means situated adjacent to the outlet and forming a portion of the fluid flow pathways, for preventing fluid flow through the device in the presence of negative hydrostatic pressure at the outlet.

12. A subcutaneously implantable shunt system, comprising:
   a shunt inlet;
   a shunt outlet;
   first valve means for controlling fluid flow from the shunt inlet to the shunt outlet;
   second valve means for controlling fluid flow from the shunt inlet to the shunt outlet;
   first fluid conduit means for directing fluid through the first and second valve means as the fluid passes through the shunt system;
   second fluid conduit means for directing fluid through the second valve means and bypassing the first valve means as the fluid passes through the shunt system; and
   means for selectively directing fluid either through the first or second fluid conduit means, the fluid directing means including a selectively positionable plug movable between a first position wherein the second fluid conduit is open to fluid flow therethrough and a second position wherein the second fluid conduit is closed to fluid flow therethrough, and a magnetically polarized, percutaneously manipulable cam rotatable between a first position and a second position, the plug having means for occluding the second fluid conduit at one end and a cam rider at another end, wherein the cam rider interacts with the cam such that rotation of the cam between its first and second positions simultaneously moves the plug between its first and second positions.

13. A shunt system as set forth in claim 12 including a pump situated between the shunt inlet and the shunt outlet, wherein the pump provides means for flushing fluid through the shunt system by application of manual percutaneous pressure to the pump.

14. A shunt system as set forth in claim 12, including means for occluding a portion of the shunt system adjacent to the inlet by application of manual percutaneous pressure to the shunt system, and means for occluding a portion of the shunt system adjacent to the outlet by application of manual percutaneous pressure to the shunt system.

15. A shunt system as set forth in claim 12, including siphon control device means situated between the second valve means and the outlet, for preventing fluid flow through the device in the absence of negative hydrostatic pressure at the outlet.

16. A shunt system as set forth in claim 12, wherein the first and second valve means each include a base having a fluid passageway therethrough and a valve seat surrounding a portion of the fluid passageway, and a flow control member which contacts the valve seat in a manner normally occluding the fluid passageway but selectively opening to permit controlled unidirectional flow therethrough.

17. A shunt system as set forth in claim 16, wherein each flow control member includes a central support and a resilient membrane, the central support being attached to the respective base and extending therefrom to support the resilient membrane, the resilient membrane being generally arch-shaped and having a portion thereof capable of engaging the respective valve seat to occlude the respective fluid passageway.

18. A shunt system as set forth in claim 13, wherein the fluid directing means is situated within the pump, the first valve means is situated between the shunt inlet and he pump, and the second valve means is situated between the pump and the shunt outlet.

19. A flow control device having selectable alternative fluid pathways, for use in a subcutaneously implanted physiological shunt system, the flow control device comprising:
a housing having an inlet and an outlet;
a flushing reservoir situated between the inlet and the outlet and having an overlying, resiliently deformable dome forming a portion of the housing, the flushing reservoir providing means for flushing fluid through the flow control device by application of percutaneous manual pressure to the device to depress the dome;
a first valve situated between the inlet and the flushing reservoir, for controlling fluid flow from the inlet to the outlet;
a second valve situated between the flushing reservoir and the outlet, for controlling fluid flow from the inlet to the outlet;
first fluid conduit means for directing fluid through the first and second valves as the fluid passes through the flow control device;
second fluid conduit means for directing fluid through the second valve and bypassing the first valve as the fluid passes through the flow control device; and
means for selectively directing fluid either through the first or second fluid conduit means, the fluid directing means including a selectively positionable plug movable between a first position wherein the second fluid conduit is open to fluid flow therethrough and a second position wherein the second fluid conduit is closed to fluid flow therethrough, and a magnetically polarized, percutaneously manipulable cam rotatable between a first position and a second position, the plug having means for occluding the second fluid conduit at one end and a cam rider at another end, wherein the cam rider interacts with the cam such that rotation of the cam between its first and second positions simultaneously moves the plug between its first and second positions.

20. A flow control device as set forth in claim 19, wherein the first and second valve means each include a base having a fluid passageway therethrough and a valve seat surrounding a portion of the fluid passageway, and a flow control member which contacts the valve seat in a manner normally occluding the fluid passageway but selectively opening to permit controlled unidirectional flow therethrough.

21. A flow control device as set forth in claim 19, including a siphon control device adjacent to the outlet, which prevents fluid flow through the flow control device in the absence of positive upstream fluid pressure through the device or in response to negative hydrostatic downstream pressure on the device.

22. A flow control device as set forth in claim 19 including means for occluding a portion of the flow control device adjacent to the inlet by application of manual percutaneous pressure to the flow control device.

23. A fluid flow control device, comprising:
a housing having an inlet and an outlet;
a first fluid flow pathway through the housing from the inlet to the outlet, the first fluid flow pathway having first means for resisting fluid flow therethrough;
a second fluid flow pathway through the housing from the inlet to the outlet, the second fluid flow pathway having second means for resisting fluid flow therethrough; and
means for selectively directing fluids through one of the first or the second fluid flow pathways, the fluid directing means being actuable by percutaneous manipulation of the device when subcutaneously implanted;
wherein the means for selectively directing fluids through either the first or the second fluid flow pathways includes means for occluding the second fluid flow pathway, comprising a selectively positionable plug movable between a first position wherein the second fluid flow pathway is open to fluid flow therethrough, and a second position wherein the second fluid flow pathway is closed to fluid flow therethrough.

24. A fluid flow control device as set forth in claim 23, wherein the means for occluding the second fluid flow pathway includes a magnetically polarized, percutaneously manipulable cam rotatable between a first position and a second position, the plug having an occluder at one end and a cam rider at another end, wherein the cam rider interacts with the cam such that rotation of the cam between its first and second positions simultaneously moves the plug between its first and second positions.

* * * * *